(12) United States Patent
Holmqvist

(10) Patent No.: US 8,876,785 B2
(45) Date of Patent: Nov. 4, 2014

(54) DELIVERY MEMBER ATTACHMENT DEVICE

(75) Inventor: Anders Holmqvist, Värmdö (SE)

(73) Assignee: SHL Group AB, Nacka Strand (SE)

( * ) Notice: Subject to any disclaimer, the term of this patent is extended or adjusted under 35 U.S.C. 154(b) by 0 days.

(21) Appl. No.: 13/139,294

(22) PCT Filed: Nov. 26, 2009

(86) PCT No.: PCT/EP2009/065903
§ 371 (c)(1),
(2), (4) Date: Aug. 12, 2011

(87) PCT Pub. No.: WO2010/066589
PCT Pub. Date: Jun. 17, 2010

(65) Prior Publication Data
US 2011/0288493 A1    Nov. 24, 2011

Related U.S. Application Data

(60) Provisional application No. 61/122,369, filed on Dec. 13, 2008.

(30) Foreign Application Priority Data

Dec. 12, 2008 (SE) .................................... 0850129

(51) Int. Cl.
| | |
|---|---|
| *A61M 5/00* | (2006.01) |
| *A61M 5/31* | (2006.01) |
| *A61M 15/00* | (2006.01) |
| *A61M 5/24* | (2006.01) |
| *A61M 5/34* | (2006.01) |
| *A61M 11/00* | (2006.01) |

(52) U.S. Cl.
CPC ............. *A61M 5/3134* (2013.01); *A61M 15/00* (2013.01); *A61M 2005/2407* (2013.01); *A61M 5/348* (2013.01); *A61M 5/347* (2013.01); *A61M 5/24* (2013.01); *A61M 11/00* (2013.01)
USPC ........... 604/240; 604/232; 604/241; 604/242; 604/243

(58) Field of Classification Search
USPC .......................................... 604/240–243, 232
See application file for complete search history.

(56) References Cited

U.S. PATENT DOCUMENTS

| | | | |
|---|---|---|---|
| 4,490,142 A | 12/1984 | Silvern | |
| 4,740,205 A | 4/1988 | Seltzer et al. | |
| 7,988,678 B2 * | 8/2011 | Monson et al. | 604/240 |
| 2009/0036843 A1 * | 2/2009 | Erskine | 604/272 |

FOREIGN PATENT DOCUMENTS

| | | | |
|---|---|---|---|
| EP | 0787501 A2 | | 8/1997 |
| GB | 470559 A | | 8/1937 |
| GB | 780775 A | * | 8/1957 |
| WO | 2008/008694 A2 | | 1/2008 |

OTHER PUBLICATIONS

EPO, Int'l Search Report in PCT/EP2009/065903, Apr. 8, 2010.
EPO, Written Opinion in PCT/EP2009/065903, Apr. 8, 2010

* cited by examiner

*Primary Examiner* — Emily Schmidt
*Assistant Examiner* — Lauren M Peng
(74) *Attorney, Agent, or Firm* — Piedmont Intellectual Property

(57) ABSTRACT

The present invention relates to a delivery member attachment device (10) comprising a neck (12) having an inner space intended to accommodate a connection part of a medicament container, which neck (12) is intended to receive a delivery member (30) for creating a passage between the medicament container via the connection part and through the delivery member, that said neck (12) is arranged with threads (14) arranged to engage with corresponding threads (34) of an attachment part (32 of said delivery member (30), and wherein said neck (12) further is arranged with a number of slits (16) providing a number of tongues (18) between said slits, and wherein said tongues (18) are arranged to flex inwards, when a delivery member (30) is to be attached, to allow an axial pushing of said attachment part (32) onto, and in engagement with, said neck (12).

8 Claims, 4 Drawing Sheets

DELIVERY MEMBER ATTACHMENT DEVICE

TECHNICAL AREA

The present invention relates to a delivery member attachment device to be used with a medicament delivery device.

TECHNICAL BACKGROUND

There are a number of different medicament delivery devices that have been developed with the aim to provide self-administration to the users. In that respect the medicament delivery devices should be easy to use, i.e. not requiring a lot of learning or reading of instruction manuals. Further, the medicament delivery devices should be easy to use regarding ease of preparing the device for drug delivery even for patients with reduced dexterity of their hands.

One step that often is required in order to have the medicament delivery device ready for medicament delivery is to attach a delivery member to the front end of the medicament delivery device. A common design of a delivery member is a pen needle for pen-type injectors. Generally the pen needles have a threaded hub that can be screwed onto and off the pen injector. When screwing onto the injector, the rear end of the needle penetrates an elastic membrane or septum of a medicament container in order to provide a passage from the container through the needle.

For some patients this screwing action can be quite difficult, especially for persons with reduced dexterity of their hands and/or persons with shaking hands that are difficult to control. These patients may not be able to attach a needle by a screwing action in order to receive a dose of medicament. Document WO 2008/008694 discloses one attempt for facilitating the attachment of a pen needle. The front end of a cartridge holder collet is arranged with a number of resilient fingers having protrusions on their outer surfaces. When a pen needle is to be attached it is pushed onto the resilient fingers whereby the internal threads of the needle engage with the protrusions of the fingers. In order to lock the engagement the collet is then pushed axially onto the neck of a medicament container, which presses the fingers against the hub of the pen needle. For removing the pen needle from the collet, the medicament container is pushed back again, whereby the fingers may be pressed inwards by the user, which releases the pen needle so that it may be dropped in a suitable safety container.

Even though it might be reasonably easy to put the pen needle onto the collet, it requires further handling in that the medicament container has to be pushed in position in order to lock the pen needle to the collet. There is a risk for patients with reduced functions of their hands or patients with uncontrolled shaking of hands that the needle falls off before the medicament container has been pushed forward in the locking position. Also, many patients are used to the screwing action both for attaching and in particular detaching the pen needle, which is not provided for with the device according to WO 2008/008694.

BRIEF DESCRIPTION OF THE INVENTION

The aim of the present invention is to remedy the drawbacks of the known delivery member attachment devices and thereby provide an attachment device that utilizes a conventional threaded delivery member as e.g. a pen needle with optionally conventional threaded attachment or snap-on attachment.

This aim is obtained by a device with the features of the independent patent claim. Preferable embodiments of the invention form the subject of the dependent patent claims.

According to a main aspect of the invention it is characterised by a delivery member attachment device to be used with a medicament delivery device, which delivery member attachment device comprises a neck having an inner space intended to accommodate a connection part of a medicament container, which neck is intended to receive an delivery member for creating a passage between the medicament container via the connection part and through the delivery member, that said neck is arranged with threads arranged to engage with corresponding threads of an attachment part of said delivery member and wherein said neck further is arranged with a number of slits providing a number of tongues between said slits, and wherein said tongues are arranged to flex inwards, when a delivery member is to be attached, to allow an axial pushing of said attachment part onto, and in engagement with, said neck.

According to another aspect of the invention, said inner space of said neck is designed such that an annular gap is provided around said connection part of said medicament container for allowing said inwards flexing of said tongues.

According to a further a further aspect of the invention, bridges are created between the tongues for increasing the flexing resistance of the tongues.

There are a number of advantages with the present invention. By the creation of slits on the threaded neck of a medicament container it is possible to attach a threaded hub of a delivery member by axial pushing of the hub onto the neck. This greatly facilitates the attachment of a delivery member on a medicament delivery device. Thus, it is no longer necessary to screw the delivery member onto the neck. However, this possibility still exists if a user prefers the screwing action. Further, the axial pushing is very simple and does not require any other actions like movement of the medicament container in order to secure the delivery member on the neck.

On the contrary, with the present invention, there is created an annular gap between the medicament container and the inner surface of the neck of the container holder in order to allow the flexing action of the tongues of the neck when the delivery member is pushed onto the neck. Further, in order to create a somewhat stiffer flexing action, or more resistance of the tongues, some bridges are arranged between the tongues. Preferably the bridges have a somewhat curved shape in order to facilitate the bending of them.

In all, a very simple attachment of the delivery member is obtained which still provides the possibility of screwing the delivery member onto the neck of the medicament holder. For removing the delivery member after medicament delivery, a conventional screwing action is performed. The screwing off of a delivery member is much easier, even for persons with reduced dexterity in their hands, than the screwing on of a delivery member.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

Figure 1:
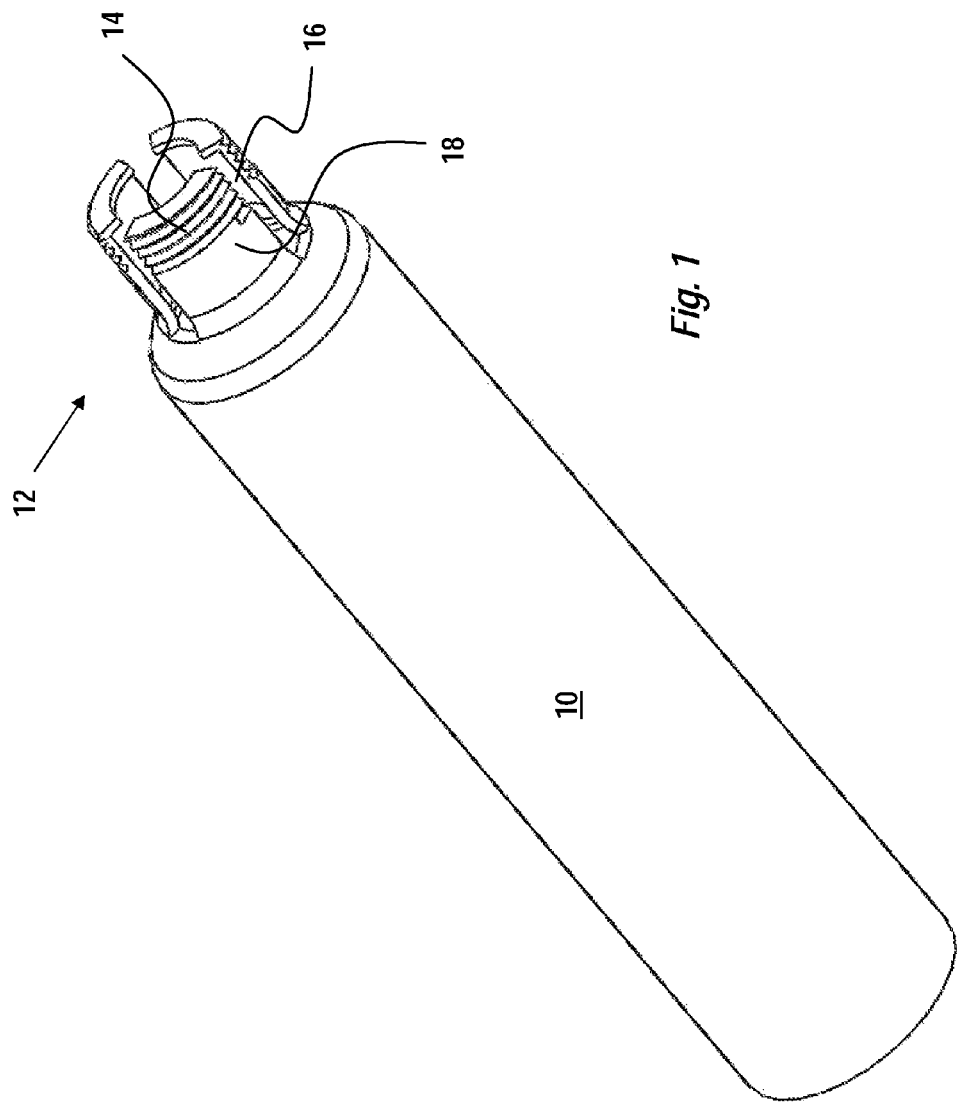
FIG. 1 is a perspective view of a first embodiment of a delivery member attachment device according to the present invention.

The present invention is intended to be used with a medicament delivery device containing a medicament container. However, these parts are not described or shown in the drawings because they do not form part of the invention, and also for purposes of clarity.

The embodiment shown in FIG. 1 comprises a delivery member attachment device 10. The device 10 is arranged with a front neck 12 provided with threads 14 and an inner space intended to accommodate a connection part 40 of a medicament container indicated by dashed lines, which neck is intended to receive a delivery member 30 for creating a passage between the medicament container via the connection part and through the delivery member. The neck is further arranged with a number of slots 16, thereby creating a number of fingers or tongues 18 that have flexible properties in the radial direction as will be described below. The inner diameter of the neck 12 is designed somewhat larger than the neck of the medicament container that is intended to be placed inside the delivery member attachment device 10 such that an annular gap is formed there between, thereby enabling flexing action of the tongues 18. The interior of the rear end of the container is arranged with a movable stopper. The delivery member attachment device is also arranged with connecting means, e.g. threads, bayonet fittings, snap-in connectors or the like, or fixedly by deep grooves, by gluing, welding or the like depending on the application and intended use, in order to be connected to a rear housing which comprises a power pack that is used for exerting a force on said stopper for expelling the medicament.

Figure 2:
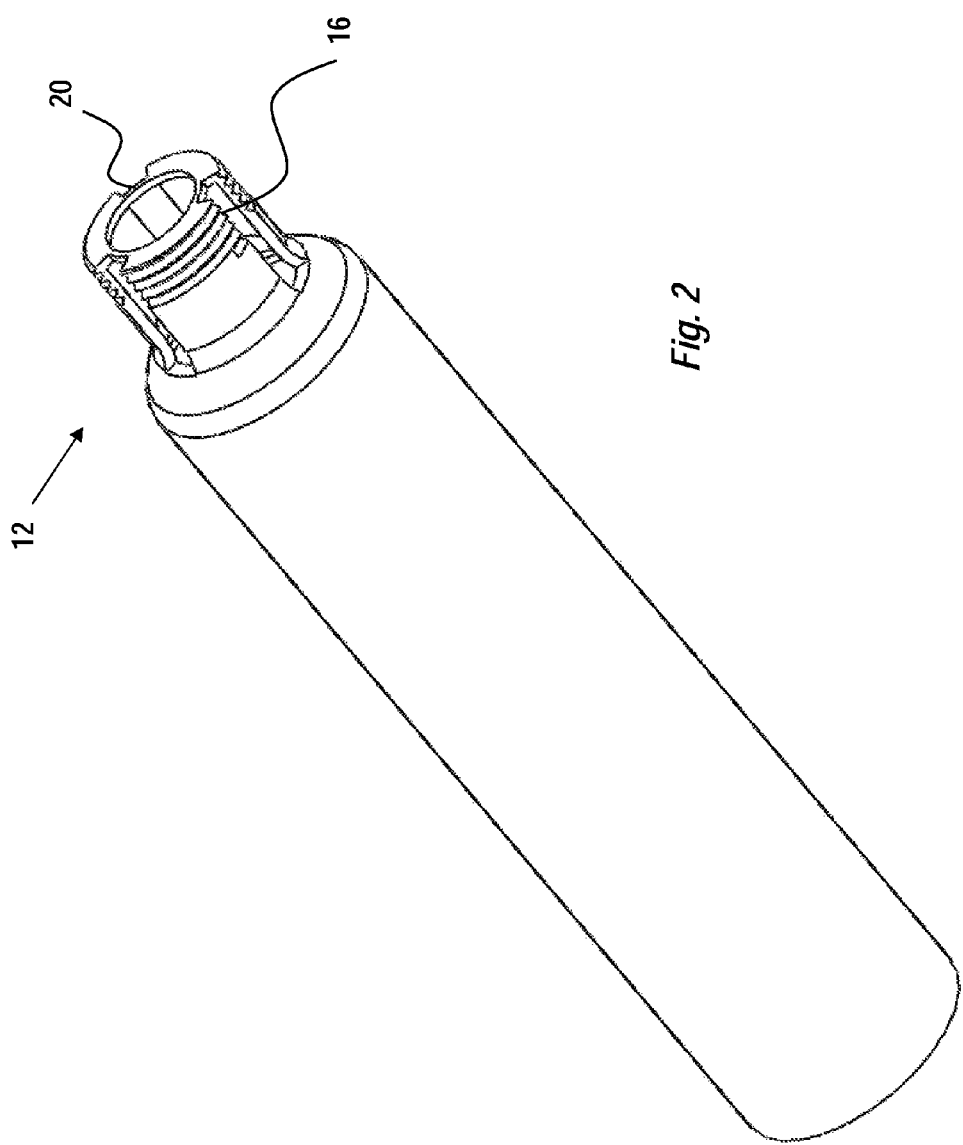
FIG. 2 is a perspective view of a second embodiment of a delivery member attachment device according to the present invention.
Figure 3:
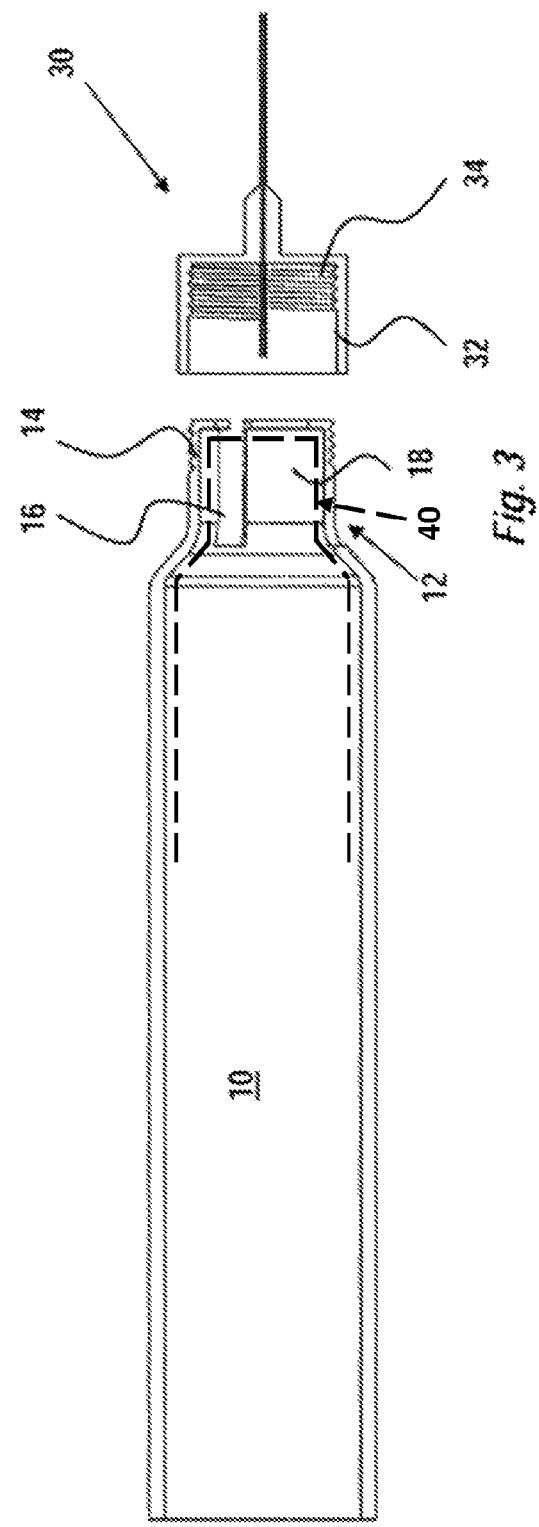
FIGS. 3 and 4 are side-views in cross-section before and after attachment of a delivery member to the delivery member attachment device according to the present invention.
Figure 4:
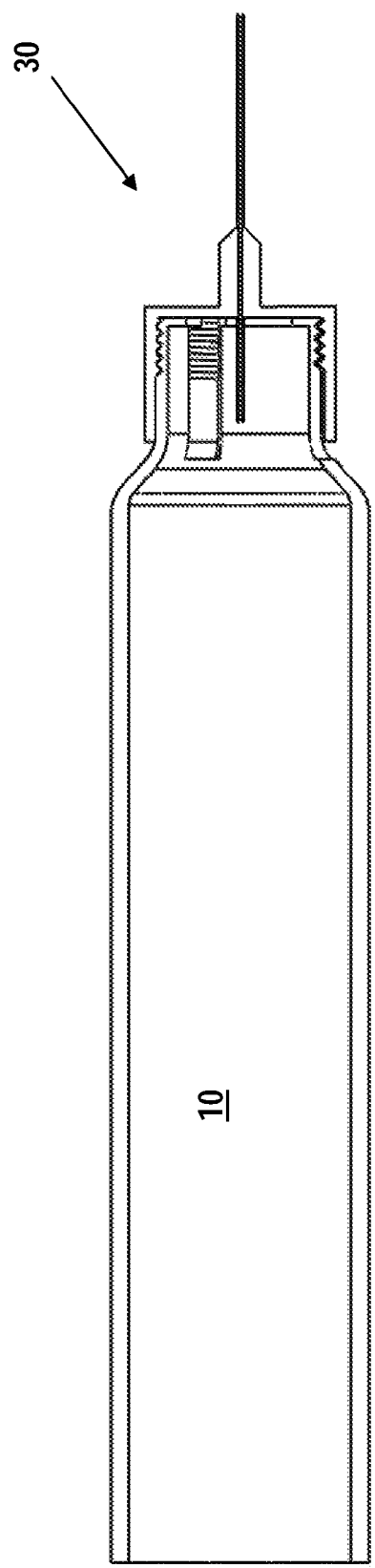

FIG. 2 shows a somewhat modified embodiment in relation to the one in FIG. 1. Here the upper ends of the slots 16 are arranged with some bridges 20. The thickness of the bridges is chosen such that they will bend somewhat when the tongues are caused to flex inwards, where the bending is facilitated by the curved shape of the bridges 20. However, the flexing properties of the bridges urge the tongues back outwards in the radial direction, creating a flexing resistance. When the delivery member 30, e.g. a pen needle as shown in FIG. 3, is to be attached to the delivery member attachment device, it can merely be pushed onto the neck of delivery member attachment device. Due to the flexing properties of the tongues 18, they will flex inwards thereby letting a hub 32 of the delivery member 30 to be attached onto the neck, whereby the threads 34 of the hub will engage with the threads 14 of the neck, FIG. 4. Due to the threads of the hub and the neck it is of course possible to screw the delivery member 30 onto the neck in the conventional manner. When the delivery member is to be removed from the delivery member attachment device 10 after a medicament delivery, it is merely screwed off from the neck in the normal manner. As mentioned earlier, the inner diameter of the neck is chosen such that the delivery member may be pushed onto the neck with a medicament container in position inside the delivery member attachment device, allowing the tongues 18 to flex inwards to such an extent that the hub 32 may be pushed in the proper position on the neck.

The wording delivery member may embrace several different types of delivery members such as pen needles, nozzles, just to mention a few. In that respect the present invention could also be used with other types of delivery devices such as powder or aerosol inhalers as well as nebulizers, with mouth pieces or nasal pieces and capable of delivering medicament to be inhaled by a patient.

Further, the wording medicament container may embrace several different types of containers such as cartridges, ampoules, vials, aerosol containers, just to mention a few. In that respect the present invention could also be used with other types of delivery devices such as powder or aerosol inhalers as well as nebulizers, with mouth pieces or nasal pieces and capable of delivering medicament to be inhaled by the patient.

It is to be understood that the embodiments described above and shown in the drawings only are to be regarded as non-limiting examples of the invention and that it may be modified in many ways within the scope of the patent claims.

The invention claimed is:

1. A delivery member attachment device for a medicament delivery device, comprising:
   a neck having an inner space for a connection part of a medicament container, wherein the neck receives a delivery member for creating a passage between the medicament container via the connection part and through the delivery member; the neck has threads arranged to engage with corresponding threads of an attachment part of the delivery member; the neck includes a number of slots providing a number of tongues between the slits; and the tongues flex inward by attachment of a delivery member to allow an axial pushing of the attachment part onto, and in engagement with, the neck; and an inner diameter of the neck is larger than the connection part such that an annular gap is formed between the neck and the connection part when the neck's inner space accommodates the connection part.

2. The delivery member attachment device of claim 1, wherein the tongues include bridges therebetween for increasing a flexing resistance of the tongues.

3. The delivery member attachment device of claim 1, wherein the inner space of the neck is such that an annular gap is provided around the connection part of the medicament container for allowing inward flexing of the tongues.

4. The delivery member attachment device of claim 3, wherein the tongues include bridges therebetween for increasing a flexing resistance of the tongues.

5. A medicament delivery device, comprising a delivery member attachment device according to claim 1.

6. The medicament delivery device of claim 5, comprising the delivery member attachment device according to claim 2.

7. The medicament delivery device of claim 5, comprising the delivery member attachment device according to claim 3.

8. The medicament delivery device of claim 5, comprising the delivery member attachment device according to claim 4.

\* \* \* \* \*